(12) United States Patent
Shaanan et al.

(10) Patent No.: US 8,292,826 B1
(45) Date of Patent: Oct. 23, 2012

(54) COCKING AND ADVANCING MECHANISM FOR ANALYTE TESTING DEVICE

(75) Inventors: Gad Shaanan, La Jolla, CA (US); Marc Goldman, San Diego, CA (US)

(73) Assignee: YofiMETER, Inc., La Jolla, CA (US)

( * ) Notice: Subject to any disclaimer, the term of this patent is extended or adjusted under 35 U.S.C. 154(b) by 0 days.

(21) Appl. No.: 13/308,315

(22) Filed: Nov. 30, 2011

Related U.S. Application Data (63) Continuation of application No. 13/188,399, filed on Jul. 21, 2011, which is a continuation-in-part of application No. 13/187,360, filed on Jul. 20, 2011, and a continuation-in-part of application No. 13/187,397, filed on Jul. 20, 2011, which is a continuation-in-part of application No. 13/165,621, filed on Jun. 21, 2011.

(51) Int. Cl.
*A61B 5/00* (2006.01)
*A61B 17/14* (2006.01)
*A61B 17/32* (2006.01)
*B65D 81/00* (2006.01)

(52) U.S. Cl. ........ 600/583; 600/575; 600/584; 606/181; 606/183

(58) Field of Classification Search ........... 600/583, 600/584, 573, 575, 576; 606/181–183; 422/410
See application file for complete search history.

(56) References Cited

U.S. PATENT DOCUMENTS

| | | | |
|---|---|---|---|
| 4,794,926 A | 1/1989 | Munsch et al. | |
| 5,196,025 A | 3/1993 | Ranalletta et al. | |
| 5,871,494 A | 2/1999 | Simons et al. | |
| 5,971,941 A * | 10/1999 | Simons et al. | 600/573 |
| 6,071,294 A | 6/2000 | Simons et al. | |
| 6,228,100 B1 * | 5/2001 | Schraga | 606/183 |
| 6,332,871 B1 | 12/2001 | Douglas et al. | |
| 6,364,889 B1 | 4/2002 | Kheiri et al. | |
| 6,468,287 B1 | 10/2002 | Baugh | |

(Continued)

FOREIGN PATENT DOCUMENTS

CA 2526543 1/2005

(Continued)

OTHER PUBLICATIONS

* "Accu-Chek Mobile System", Blood Glucose Meter, Roche LTD., Feb. 23, 2011, http://www.accu-check.co.uk/gb/products/metersystems/mobile.html.

(Continued)

*Primary Examiner* — Max Hindenburg
*Assistant Examiner* — John Pani
(74) *Attorney, Agent, or Firm* — Fish & Associates, PC (57) ABSTRACT

An analyte testing device includes an analyte sensor, a lancet, and a mechanism with an actuator that operates to independently expose the analyte sensor and advance the lancet into position for use. The analyte sensor is preferably included in an analyte sensor cartridge that houses a plurality of sensors. Similarly, the lancet is preferably included in a lancet cartridge that houses a plurality of lancets. The actuator can be a lever configured to expose the analyte sensor and advance the lancet into position with a single motion (e.g., pulling the lever). The actuator also preferably operates to cock a hammer in preparation for lancing a body member to draw a blood sample. The mechanism can be a linkage coupled with the actuator and configured to engage the analyte sensor and lancet.

18 Claims, 7 Drawing Sheets

U.S. PATENT DOCUMENTS

| | | |
|---|---|---|
| 6,472,220 B1 | 10/2002 | Simons et al. |
| 6,616,616 B2 | 9/2003 | Fritz et al. |
| 6,783,537 B1 | 8/2004 | Kuhr et al. |
| 6,827,899 B2 | 12/2004 | Maisey et al. |
| 6,849,237 B2 | 2/2005 | Housefield et al. |
| 6,872,358 B2 | 3/2005 | Hagen et al. |
| 6,997,343 B2 | 2/2006 | May et al. |
| 7,025,774 B2 | 4/2006 | Freeman et al. |
| 7,175,642 B2 | 2/2007 | Briggs et al. |
| 7,192,405 B2 | 3/2007 | DeNuzzio et al. |
| 7,211,096 B2 | 5/2007 | Kuhr et al |
| 7,258,693 B2 | 8/2007 | Freeman et al. |
| 7,261,691 B1 | 8/2007 | Asomani |
| 7,344,507 B2 | 3/2008 | Briggs et al. |
| 7,430,825 B2 | 10/2008 | Vanek et al. |
| 7,582,063 B2 | 9/2009 | Wurster et al. |
| 7,662,065 B1 | 2/2010 | Kahn et al. |
| 7,785,338 B2 | 8/2010 | Kuhr et al. |
| 7,848,765 B2 | 12/2010 | Phillips et al. |
| 7,883,015 B2 | 2/2011 | Ackermann et al. |
| 7,887,682 B2 | 2/2011 | Wang et al. |
| 7,892,183 B2 | 2/2011 | Boecker et al. |
| 7,892,185 B2 | 2/2011 | Freeman et al. |
| 7,914,742 B2 | 3/2011 | Arbogast et al. |
| 7,922,971 B2 | 4/2011 | Bryer et al. |
| 7,935,063 B2 | 5/2011 | Roe |
| 7,951,114 B2 | 5/2011 | Rush et al. |
| 7,955,791 B2 | 6/2011 | Dinello et al. |
| 2002/0170823 A1 | 11/2002 | Housefield et al. |
| 2002/0177761 A1 | 11/2002 | Orloff et al. |
| 2003/0083685 A1 | 5/2003 | Freeman et al. |
| 2003/0153900 A1 | 8/2003 | Aceti et al. |
| 2003/0191415 A1* | 10/2003 | Moerman et al. ............ 600/584 |
| 2004/0044272 A1 | 3/2004 | Moerman et al. |
| 2004/0127819 A1* | 7/2004 | Roe ............................... 600/583 |
| 2004/0172284 A1 | 9/2004 | Sullivan et al. |
| 2005/0015020 A1* | 1/2005 | LeVaughn et al. ............ 600/583 |
| 2005/0238538 A1 | 10/2005 | Braig et al. |
| 2006/0229502 A1 | 10/2006 | Pollock et al. |
| 2006/0245131 A1 | 11/2006 | Ramey et al. |
| 2006/0279431 A1 | 12/2006 | Bakarania et al. |
| 2006/0281187 A1 | 12/2006 | Emery et al. |
| 2007/0007183 A1 | 1/2007 | Schulat et al. |
| 2007/0073590 A1 | 3/2007 | Cosentino et al. |
| 2007/0088271 A1 | 4/2007 | Richards |
| 2007/0179404 A1 | 8/2007 | Escutia et al. |
| 2008/0139910 A1 | 6/2008 | Mastrototaro et al. |
| 2008/0167578 A1 | 7/2008 | Bryer et al. |
| 2008/0200838 A1 | 8/2008 | Goldberger et al. |
| 2008/0217407 A1 | 9/2008 | Ackermann et al. |
| 2009/0010802 A1 | 1/2009 | Joseph et al. |
| 2009/0138207 A1 | 5/2009 | Cosentino et al. |
| 2009/0171589 A1 | 7/2009 | Kovatchev |
| 2009/0270765 A1 | 10/2009 | Ghesquiere et al. |
| 2009/0322513 A1 | 12/2009 | Hwang et al. |
| 2010/0069730 A1 | 3/2010 | Bergstrom et al. |
| 2010/0087754 A1* | 4/2010 | Rush et al. .................... 600/583 |
| 2010/0151488 A1 | 6/2010 | Smith et al. |
| 2010/0212675 A1 | 8/2010 | Walling et al. |
| 2010/0218132 A1 | 8/2010 | Soni et al. |
| 2010/0270149 A1 | 10/2010 | Wang et al. |
| 2010/0286563 A1 | 11/2010 | Bryer et al. |
| 2010/0312137 A1 | 12/2010 | Gilmour et al. |
| 2010/0317935 A1 | 12/2010 | Roe et al. |
| 2010/0331653 A1 | 12/2010 | Strafford |
| 2011/0009775 A1 | 1/2011 | Roe |
| 2011/0040165 A1 | 2/2011 | Williams, III |
| 2011/0118771 A1 | 5/2011 | Ruan et al. |
| 2011/0124130 A1 | 5/2011 | Wagner et al. |
| 2011/0124996 A1 | 5/2011 | Reinke et al. |
| 2011/0132759 A1 | 6/2011 | Petyt et al. |

FOREIGN PATENT DOCUMENTS

| | | |
|---|---|---|
| CA | 2544953 | 10/2006 |
| CA | 2599573 | 11/2006 |
| CA | 2607437 | 12/2006 |
| CA | 2646279 | 10/2007 |
| CA | 2669302 | 6/2008 |
| CA | 2327127 | 8/2010 |
| EP | 1399059 | 8/2006 |
| EP | 1717942 | 11/2006 |
| EP | 1328192 | 1/2011 |
| EP | 2284747 | 2/2011 |
| EP | 1664783 | 5/2011 |
| EP | 2195050 | 5/2011 |
| WO | 02/094092 | 11/2002 |
| WO | 03/047426 | 6/2003 |
| WO | 2006/122741 | 11/2006 |
| WO | 2006/133435 | 12/2006 |
| WO | 2007/112034 | 10/2007 |
| WO | 2008069932 | 6/2008 |
| WO | 2009146379 | 12/2009 |
| WO | 2010009870 | 1/2010 |
| WO | 2010049669 | 5/2010 |
| WO | 2010054205 | 5/2010 |
| WO | 2010068617 | 6/2010 |
| WO | 2010120563 | 10/2010 |
| WO | 2010134969 | 11/2010 |
| WO | 2011008520 | 1/2011 |
| WO | 2011/019657 | 2/2011 |
| WO | 2011/026053 | 3/2011 |
| WO | 2011/060923 | 5/2011 |

OTHER PUBLICATIONS

* "Always Connected, Always Monitoring the Critical Signals You Need to Know", CST Critical Signal Technologies, your Link to Life, Farmington Hills, MI 48335.
* Amy T., "Lifescan's New Diabetes iPhone App", Diabetes Mine: the all things diabetes blog, Mar 17, 2009, http://www.diabetesmine.com/2009/03/lifescans-new-diabetes-iphone-app.html.
* "Medline Docking Station for Glucose Meter", http://www.google.com/products/catalog?q=docking+station+for+glucose+meter&hl=en&um=1&ie=UTF-8&tbm=shop&cid=14673613440805108352&sa=X&ei=Eq-DTp2QGcnKiALyt-XwBw&ved=0CFIQ8wlwAA#.
* "OneTouch Ultra Link" Lifescan Consumer Products, 2011, http://www.lifescan.com/products/meters/ultralink/.
* "Precision PCx Glucose Monitoring System—Medline and Abbott Diabetes Care Post Acute Care Bring You Fill Billing Capture, Compliance, and Accuracy in Blood Glucose Testing", Med Supplies Care, 2011, http://www.medsuppliescare.com/medsupply.cfm/DOCKING-STATION-FOR-PRECISION-PCX-5650.
* "TRUEmanager—Track a healthier course to diabetes management", Nipro Diagnostics, 2010, http://www.niprodiagnostics.com/our_products/ma_true_manager.aspx.
* "TRUEresult Docking Station and USB Cable", Diabetes Health Supplies, 2011, http://www.diabeteshealthsupplies.com/products/TRUEresult-Docking-Station-and-USB-Cable.html.

* cited by examiner

REST POSITION

LEVER PULLED TO
COCK HAMMER AND
ADVANCE CASSETTE
TO NEXT LANCET

COCKED AND READY

BUTTON IS PRESSED
TO RELEASE HAMMER
AND PROJECT LANCET

COCKING AND ADVANCING MECHANISM FOR ANALYTE TESTING DEVICE

This application is a continuation of U.S. patent application Ser. No. 13/188,399 filed on Jul. 21, 2011, which is a continuation-in-part of U.S. patent application Ser. Nos. 13/187,360 and 13/187,397 both filed Jul. 20, 2011, which are continuation-in-parts of U.S. patent application Ser. No. 13/165,621 filed Jun. 21, 2011, all of which are incorporated herein by reference in their entirety.

FIELD OF THE INVENTION

The field of the invention is analyte testing devices.

BACKGROUND

Analyte testing devices play a critical roll in modern diagnosis and management of health-related issues. For example, a sample of human blood, urine, and/or saliva can be tested for glucose, fructosamine, hematocrit, hemoglobin blood oxygen saturation, lactates, iron, pH, cholesterol, liver enzymes (AST, ALT, alkaline phosphatase/GGT, LDH, bilirubin, etc), hormones, and other compounds.

For many diabetic patients, monitoring glucose levels and administering appropriate insulin dosages is a daily activity that requires a significant amount of time and mental energy. Current glucose meters and lancing devices often involve multiple devices, components, and supplies, and require numerous steps to monitor glucose levels. For example, conventional glucose monitoring systems may require numerous steps involving reading a test strip, readying a lancet, using the lancet, putting blood on the test strip and inserting the strip into the glucose meter, reading data from a meter, recording the data in a journal and remembering to bring the journal to the next doctor visit, and then putting away the strip and lancet packages, disposing of loose components, and storing the glucose meter. Thus, there is a need to reduce steps and simplify devices and supplies for monitoring analytes. Other needs include a compact analyte testing device and hands-free disposal of test strips.

Several known prior art references are directed at simplifying the devices and processes for monitoring analytes. Significantly, however, the prior art systems each appear to address only a subset of the convenience issues. U.S. Pat. No. 6,472,220 to Simons, for example, discloses an integrated lancing device and glucose meter. The device holds a cassette that stores a plurality of lancets and test strips. Each lancet is paired with a test strip into a single integrated unit, thus simplifying the number of separate supply components. Unfortunately, the test strip-lancet unit contemplated in Simons prevents the user from using lancets independently of the test strips.

Simons, and all other extrinsic materials discussed herein, are incorporated by reference in their entirety. Where a definition or use of a term in an incorporated reference is inconsistent or contrary to the definition of that term provided herein, the definition of that term provided herein applies and the definition of that term in the reference does not apply.

U.S. Pat. No. 7,192,405 to DeNuzzio also provides an integrated lancet-test strip unit, similar to Simons. DeNuzzio suffers from the same drawbacks as Simons.

U.S. Pat. No. 7,582,063 to Wurster discloses a glucose meter that includes a plurality of analyte sensors and a plurality of lancets on the same carrier. Each time a new blood test is performed, the carrier is rotated into position, which simultaneously exposes an analyte sensor, advances a lancet for use, and cocks a spring to operate the pre-positioned lancet. Since the analyte sensors and lancets are rotated together on the same carrier, exposing of an analyte sensor is not independent of advancing a lancet. That can be a disadvantage to a user who might want to use more than one sensor for a given stick (or for example where two different readings are desired), or might need to use two or more lancets to secure an adequate sample for a single sensor.

Wurster is also designed such that during use, the operative sensor is immediately adjacent (indeed surrounds) the operative lancet tip. That design could be viewed as being inherently problematic because the sensor will tend to sense components in the first amount of blood that is drawn. To avoid that problem it would be more desirable to expose the analyte sensor at a position at least several millimeters away from where the lancet is projected from the housing.

U.S. Pat. No. 4,794,926 to Munsch discloses a lancing device that holds a cartridge with a plurality of lancets. Rotating the cartridge in the lancing device simultaneously loads the next lancet into position for ejection while "cocking" the lancet for ejection. However, Munsch fails to integrate the lancing device with a glucose meter, and also fails to partially expose a test strip when the lancet cartridge is rotated.

U.S. Pat. Nos. 7,922,971, 6,997,343, 7,211,096, and 6,616,616 are other examples of known references that attempt to simplify methods and devices for monitoring glucose levels.

The POGO™ System by Intuity Medical, Inc. (see http://www.presspogo.com/pogo/system/) is a commercially available glucose and lancing device that is designed to simplify glucose monitoring. While the POGO™ System reduces the steps and components required, and is an improvement over many other systems, the POGO system fails to provide a separate lancet cartridge and test strip cartridge. As such, the user cannot use lancets independently of test strips.

It has yet to be appreciated that an analyte testing device can house a plurality of analyte sensors and a plurality of lancets, where a single operation of an actuator can expose an analyte sensor while advancing a lancet for projection for use, where the sensors are exposed at a distance of at least several millimeters from where the lancets are projected, and/or where the sensors and lancets can be operated independently from each other.

SUMMARY OF THE INVENTION

The inventive subject matter provides apparatus, systems, and methods in which an analyte testing device can house a plurality of analyte sensors and a plurality of lancets, where a single operation of an actuator can eject an analyte sensor while advancing a lancet for projection for use.

In some aspects of preferred embodiments, the analyte sensor is included in an analyte sensor cartridge. The cartridge preferably holds a plurality of analyte sensors. In other aspects of preferred embodiments, each analyte sensor is disposed in a test unit (e.g., a test strip).

In yet other aspects of some preferred embodiments, the lancet is included in a lancet cartridge. The lancet cartridge preferably holds a plurality of lancets.

In other aspects of preferred embodiments, the actuator comprises a manually operated lever. In some embodiments, the mechanism is entirely manually operated. In other embodiments, the mechanism is operated at least in part by a motor.

In some aspects of preferred embodiments, the mechanism includes a hammer, and the actuator operates to cock the hammer. For example, the hammer can be spring loaded and then released to eject a lancet for drawing a blood sample.

In yet other aspects of preferred embodiments, the mechanism has a linkage that exposes the analyte sensor, advances the lancet for use, and cocks the hammer, all in a single motion of the actuator. In some embodiments, the single motion comprises pulling a lever. In some embodiments the mechanism includes a first link that exposes the analyte sensor, and a second link, different from the first link, that advances the advancing the lancet. Exposing of the analyte sensor is preferably done independently relative to advancing the lancet. For example, the mechanism can include a disengagement control that is capable of disengaging the actuator from either exposing the analyze sensor or advancing the lancet.

In some aspects of preferred embodiments, the sensors are ejected at a distance of at least several millimeters from where the lancets are projected. In other aspects, the sensors and lancets can be operated independently from each other. For example, the sensors and lancets are each stored in a separate cartridge and the cartridges couple with the analyte testing device independently of one another.

Various objects, features, aspects, and advantages of the inventive subject matter will become more apparent from the following detailed description of preferred embodiments, along with the accompanying drawing figures in which like numerals represent like components.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Figures 1, 2, 3, 4:
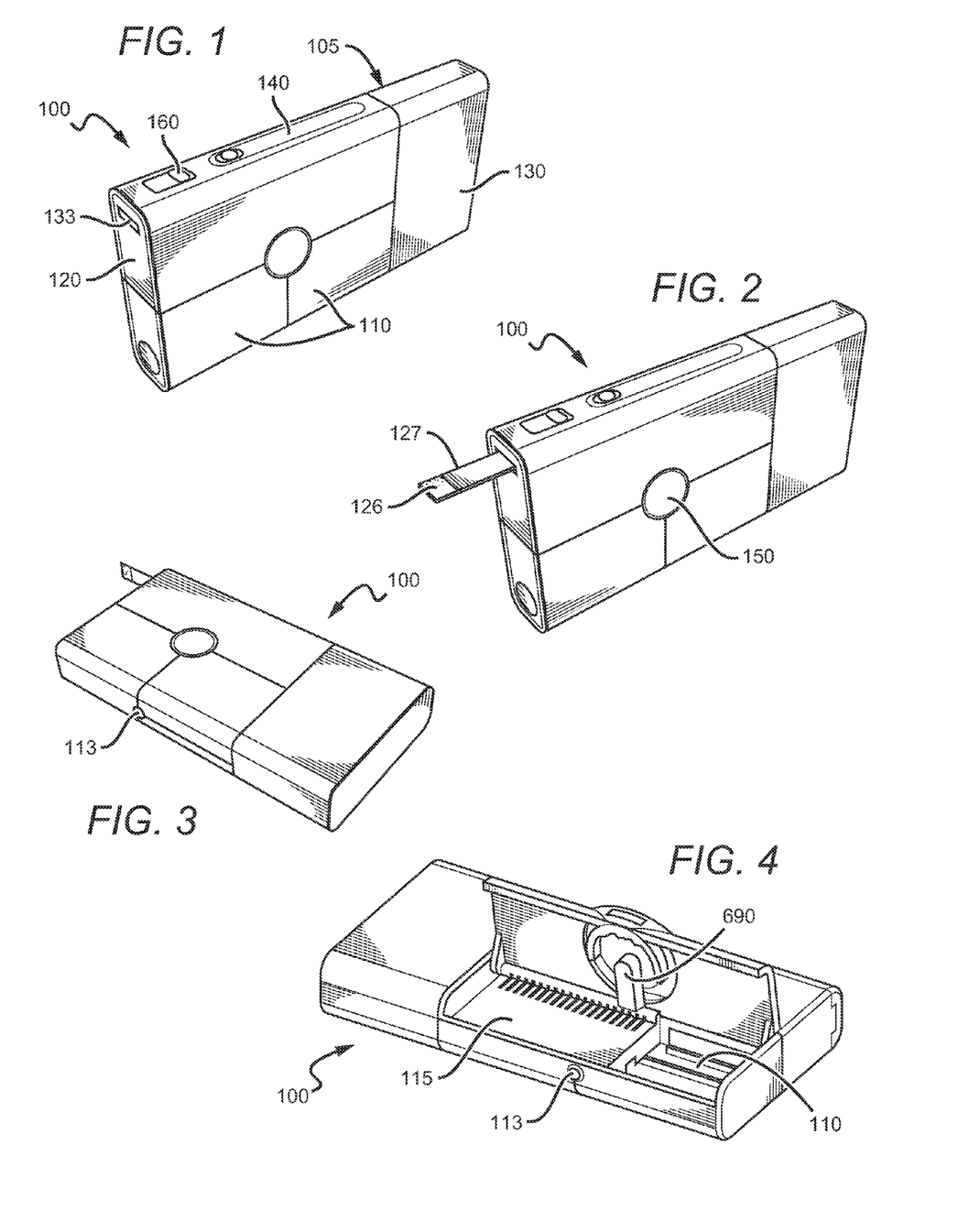
FIG. 1 is a top perspective view of one embodiment of an analyte testing device.
FIG. 2 is the device of FIG. 1, wherein an analyte sensor of a test unit has been exposed.
FIG. 3 is a bottom perspective view of the device of FIG. 1.
FIG. 4 is a back perspective view the device of FIG. 1.

FIG. 1 shows an analyte testing device 100. The housing 105 of device 100 has a first compartment 110 and a second compartment 120, for storing a lancet cartridge 115 (see FIGS. 5-7) and an analyte sensor cartridge 125 (see FIGS. 8-9). Device 100 also has an electronics compartment 130 for housing conversion electronics 137 (see FIG. 12). Conversion electronics 137 are communicatively coupled to an analyte sensor 126 (see FIGS. 8 and 10) within cartridge 125. Conversion electronics 137 is configured to convert a signal from analyte sensor 126 into readable data (e.g., glucose levels).

Device 100 has an actuator 140 comprising a lever. Actuator 140 is configured to (i) ready a lancing device (e.g., cock a hammer, see FIGS. 11 and 14), (ii) expose an analyte sensor (see FIGS. 2 and 14), and (iii) advance a lancet cartridge for use (see FIGS. 11 and 13). Device 100 also has a test unit ejector 160, which advantageously allows for hands-free disposal of a used test strip.

The housing of device 100 can be made of plastic, metal, composite, or any other material with structural and mechanical properties suitable for housing a lancet cartridge, test strip cartridge, electronics, and a linkage mechanism. Device 100 is preferably compact, with a height no more than 50 mm, a width no more than 17 mm, and a length no more than 100 mm. In especially preferred embodiments, the height is no more than 40 mm, a width is no more than 12 mm, and a length is no more than 75 mm. In some preferred embodiments, the housing of device 100 comprises an outer protective shell made of molded plastic and an inner desiccant liner to minimize exposure to moisture.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

FIG. 2 shows device 100 after actuator 140 has been cocked. The cocking of actuator 140 has caused a test unit 127 to be partially ejected from slot 133, thus exposing analyte sensor 126 (see FIGS. 8 and 10). Once actuator 140 has been cocked, a lancing device within device 100 can be projected by pressing button 150, causing one of a plurality of lancets 117 (see FIGS. 5 and 6) to exit from hole 113 (see FIG. 3). Hole 113 and slot 133 are separated by a substantial distance (more than 5 mm), thus allowing a user to bleed out an initial amount of blood before applying a blood sample to an analyte sensor. The operation of device 100 will become more apparent from a discussion of FIGS. 11-14.

FIG. 4 shows a back perspective view of device 100. A door on the backside of device 100 has been opened to reveal compartment 110. A lancet cartridge 115 is disposed within compartment 110. Device 100 has a spring-loaded return slider 690, which is configured to retract a lancet back into cartridge 115 after the lancet has been partially ejected for drawing a blood sample.

Figure 5:
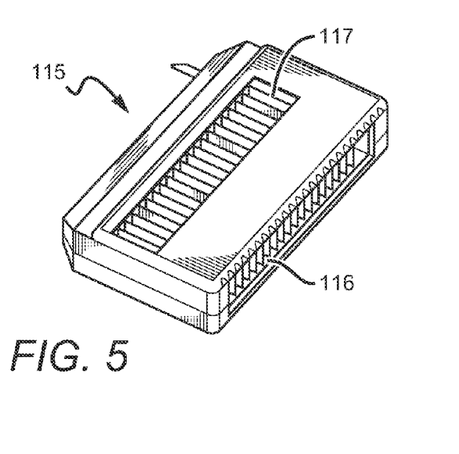
FIG. 5 is a perspective views of one embodiment of a lancet cartridge.
Figure 6:
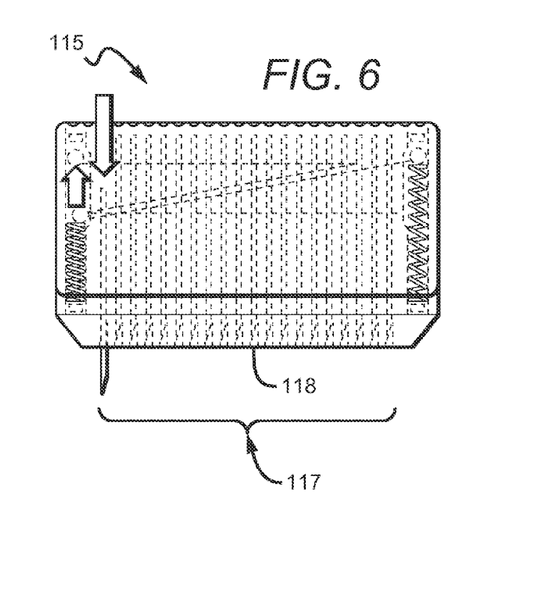
FIG. 6 is a side view of the lancet cartridge of FIG. 5.
Figure 7:
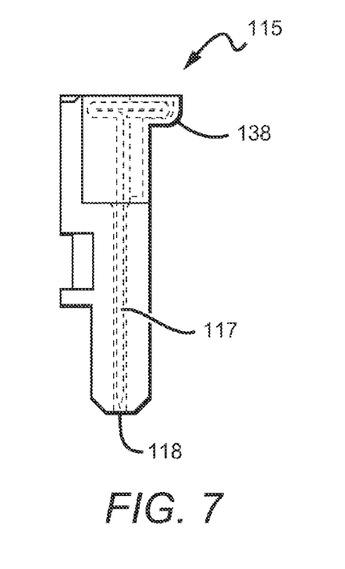
FIG. 7 is a side view of the lancet cartridge of FIG. 5.

FIGS. 5-7 show different views of a lancet cartridge 115. Cartridge 115 holds a plurality of lancets 117. A slot 116 is disposed on a side of cartridge 115, so that a hammer 186 (see FIGS. 11-14) of a lancing device within device 100 can contact one of the plurality of lancets 117, thus causing the lancet to partially exit cartridge 115 via slot 118. The lancet is retracted by return slider 690 of device 100 (see FIG. 4). Cartridge 115 also has a molded bump 138 that provides friction to the plurality of lancets 117 and helps to maintain each lancet stationary when not being fired.

Cartridge 115 can include any appropriate number of lancets, preferably between 15 and 25 lancets, more preferably between 18 and 22 lancets, and most preferably 20 lancets. The lancets are preferably sterilized and sealed prior to use.

Figure 8:
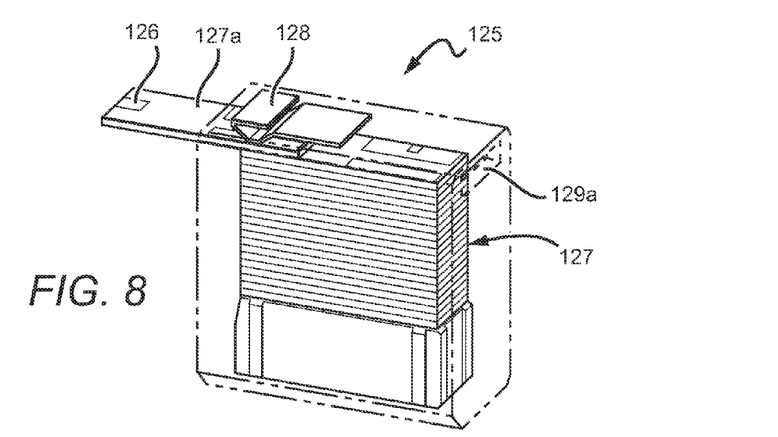
FIG. 8 is a perspective view of one embodiment of an analyte sensor cartridge.
Figure 9:
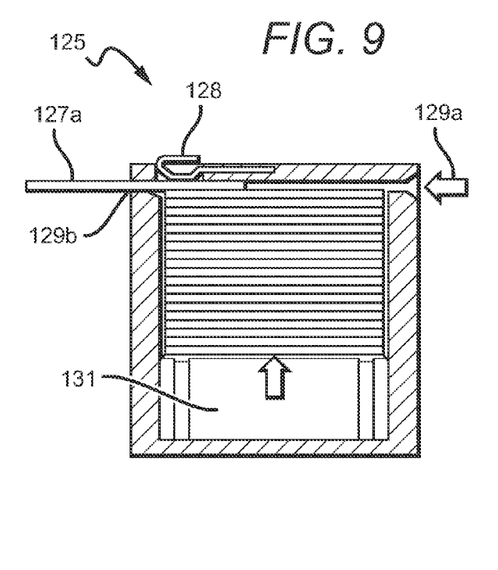
FIG. 9 is a side view of the analyte sensor cartridge of FIG. 8.

FIGS. 8 and 9 show different views of a analyte sensor cartridge 125. Cartridge 125 holds a plurality of test units 127 (e.g., test strips). Cartridge 125 has electrical contacts 128 for communicatively coupling the analyte sensors to the conversion electronics 137. Alternatively, contacts 128 could be eliminated and electronics 137 could directly interface with contacts 129 of test unit 127 (see FIG. 10) via an open aperture in cartridge 125. Cartridge 125 also has a slot 129a that couples with a test unit lateral ejection mechanism of device 100. When actuator 140 is cocked, the advance mechanism enters slot 129a and pushes a portion of test unit 127a out of slot 129b, thus exposing analyte sensor 126 for use.

Cartridge 125 can include any appropriate number of test strips, preferably between 15 and 25 test strips, more preferably between 18 and 22 test strips, and most preferably 20 test strips.

Cartridge 125 also has a spring-load base 131 configured to push the plurality of test strips 127 upward, thus repositioning a new test strip into place after test strip 127a is removed from cartridge 125.

Figure 10:
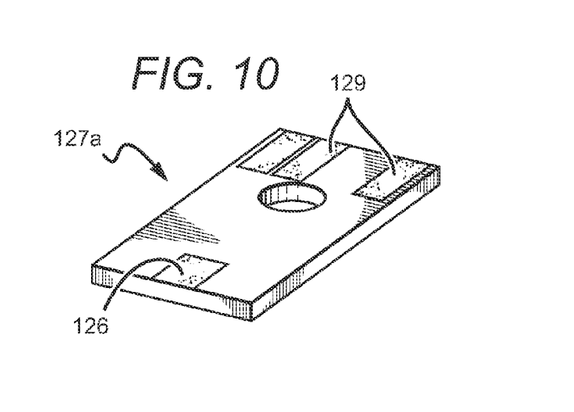
FIG. 10 is a perspective view of one embodiment of a test unit that has an analyte sensor.

FIG. 10 shows a test unit 127a having an analyte sensor 126. Analyte sensors are well known and generally comprise an absorbent material with an analyte-binding reactant. While test unit 127a is configured as a test "strip", those of skill in the art will appreciate that other shapes and configurations (e.g., capsules, disks) can be used consistently with the inventive subject matter. Analyte sensor 126 is configured to generate a signal that is sent to electrical contacts 129. Electrical contacts 129 are communicatively coupled with electrical contacts 128 of cartridge 125 and allows the signal generated by analyte sensor 126 to reach the conversion electronics 137 for analysis. Alternatively, electrical contacts 129 could directly interface with conversion electronics 137 via an open aperture on cartridge 125.

Figure 11:
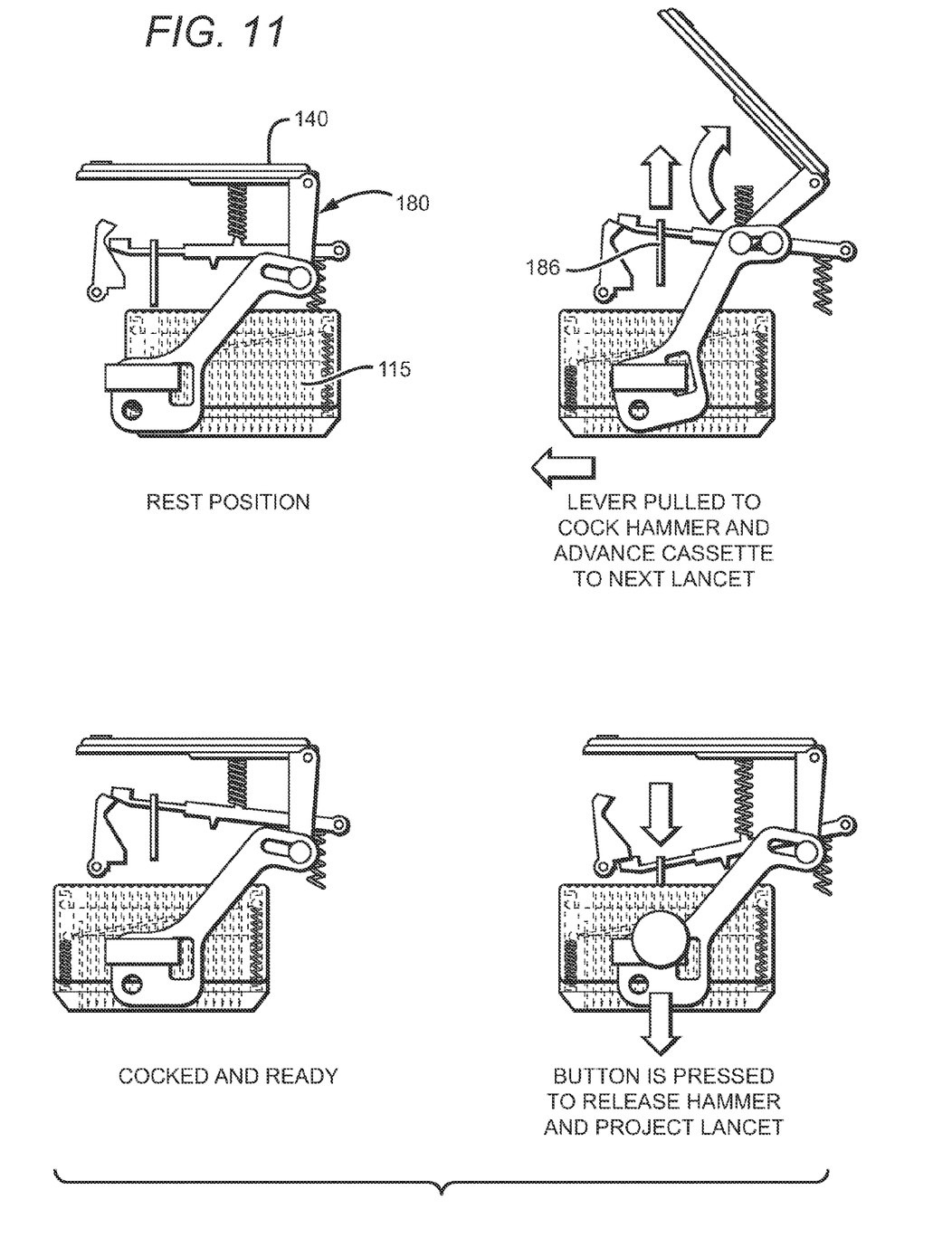
FIG. 11 shows one embodiment of a linkage mechanism of the device of FIG. 1 engaged with the lancet cartridge of FIG. 5. The linkage mechanism is shown at four different stages of use: (i) rest position; (ii) lever pulled; (iii) lever released (cocked and ready); and (iv) button pressed to project hammer.

FIG. 11 shows a linkage mechanism 180 of device 100 coupled with lancet cartridge 115. FIG. 11 provides a summary of the four progressive stages for using linkage 180 and lancet cartridge 115 as a lancing device: (i) initial resting position; (ii) cocking of actuator 140; (iii) cocked and ready position; and (iv) releasing and projecting a lancet. At the final stage, a finger or other body part can be placed over hole 113 in order to prick the body part and draw a blood sample. These four stages will now be explained in more detail.

Figure 12:
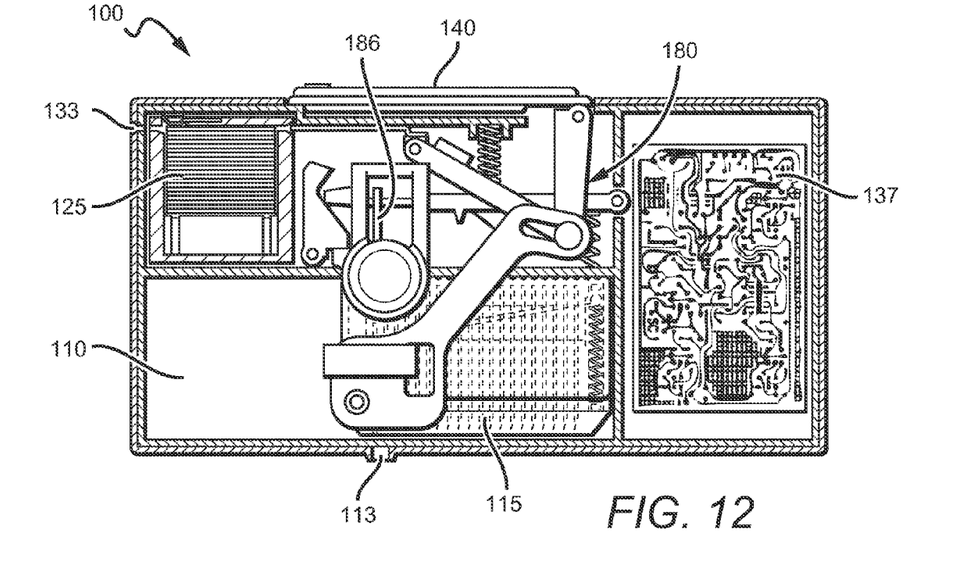
FIG. 12 is a side view of the device of FIG. 1, showing the inner components of the device in a rest position.

FIG. 12 is a side view of device 100 showing various internal components of device 100, such as: electronics 137, linkage mechanism 180, cartridge 115, and cartridge 125. FIG. 12 shows device 100 at a resting position (i.e., before actuator 140 has been cocked). Hammer 186 is in an uncocked position.

Figure 13:
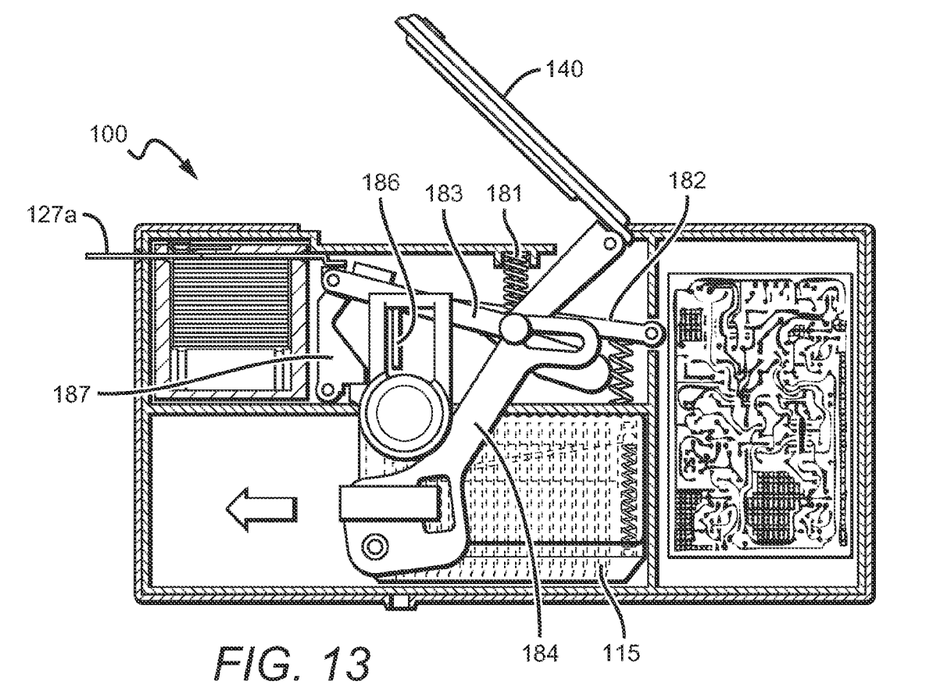
FIG. 13 is a side view of the device of FIG. 1, showing the inner components of the device as a lever is being pulled.

FIG. 13 shows the internal components of device 100 as actuator 140 is being cocked. The cocking of actuator 140 has caused link 182 to raise up and compress spring 181. At the same time, hammer 186 has been raised via link 183. In addition, the left end of link 182 has been raised over the top of link 187 such that link 182 is maintained in an inclined position and spring 181 is maintained in a compressed position (i.e., hammer 186 has been "cocked" or "readied"). At the same time, link 183 is driven to the left, pushing test strip 127a out of slot 133 (see FIG. 1). In addition, link 184 has been advanced to the left, causing cartridge 115 to advance left and into position. In preferred embodiments, link 183 couples with cartridge 115 such that when cartridge 115 has been completely advanced to the left, link 183 allows the last lancet of cartridge 115 to remain in a usable (i.e., projectable) position. For example, link 183 could release (e.g., de-couple) from cartridge 115 during subsequent cocking of actuator 140. In this manner, linkage mechanism 180 allows a lancet to be available for use, even after cartridge 115 has been advanced through each of the plurality of lancets 117.

In this manner, actuator 140 and linkage mechanism 180 are configured to (i) cock a lancing device (e.g., lift hammer 186, link 182, and spring 181) (ii) partially expose an analyte sensor on a test unit; and (iii) advance a lancet cartridge into position, all in a single motion (e.g., pulling up actuator 140). It is also contemplated that an analyte testing device could have a linkage mechanism that is configured to accomplish the three steps above using two or more motions (e.g., pulling a lever, then pushing a lever).

Figure 14:
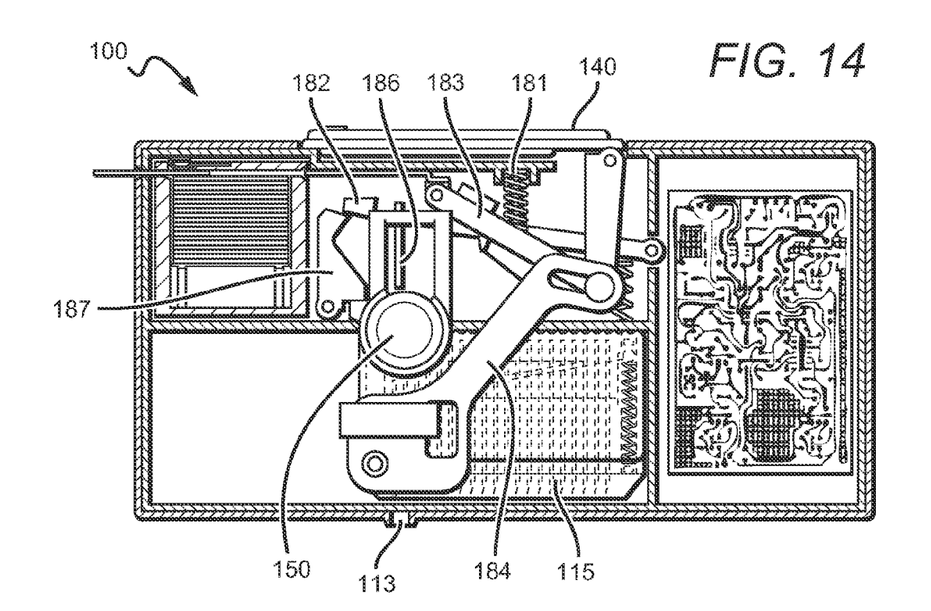
FIG. 14 is a side view of the device of FIG. 1, showing the inner compartments of the device after a lever has been pulled and a hammer has been spring-loaded.

FIG. 14 shows the position of linkage 180 after actuator 140 has been cocked. Once actuator 140 has been cocked, button 150 can be pressed to release link 187 from under link 182, thus causing spring 181 to push link 182 and hammer 186 downward to project a lancet from cartridge 115.

One of skill in the art will appreciate that configurations of linkage mechanism 180 other than that shown in the drawings can be used consistently with the inventive subject matter taught herein. In some alternative embodiments, linkage mechanism 180 is controlled and/or actuated by electrical drivers rather than pure mechanical means. For example, pulling actuator 140 could send an electrical signal to conversion electronics 137, which then operates a motor, or multiple motors, in order to perform any combination of: (i) cocking a lancing device, (ii) partially exposing a test strip for use, and (iii) advancing a lancet cartridge into position. In yet other embodiments, the lancing system is designed such that a cocking step is not required.

Figure 15:
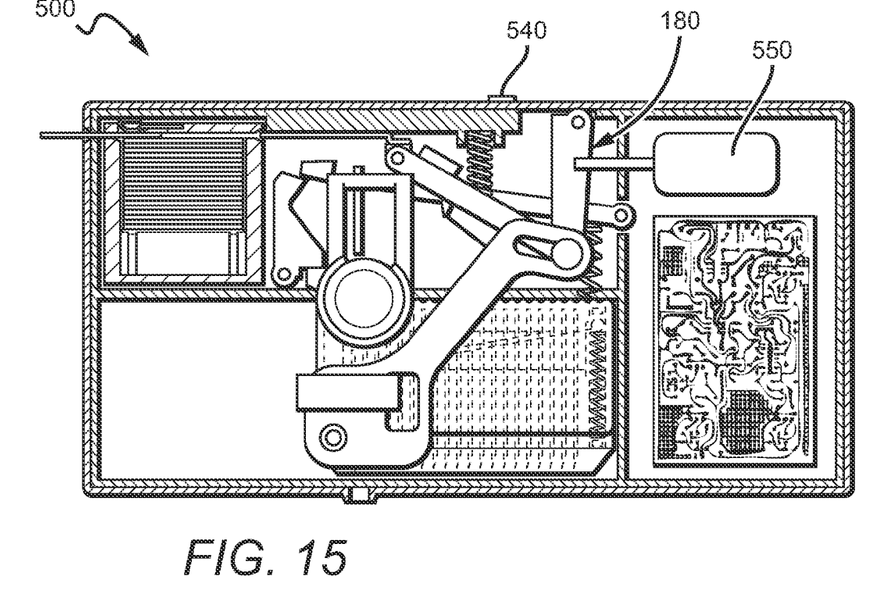
FIG. 15 is a side view of an analyte device with a motor.

FIG. 15 shows an analyte testing device 500 that has an actuator 540 and a motor 550. Actuator 540 comprises a button that sends a signal to motor 550. Motor 550 operates to drive linkage mechanism 180 upon receiving a signal. Motor 550 and actuator 540 is one embodiment of an analyte testing device that is not purely mechanism.

Figure 16:
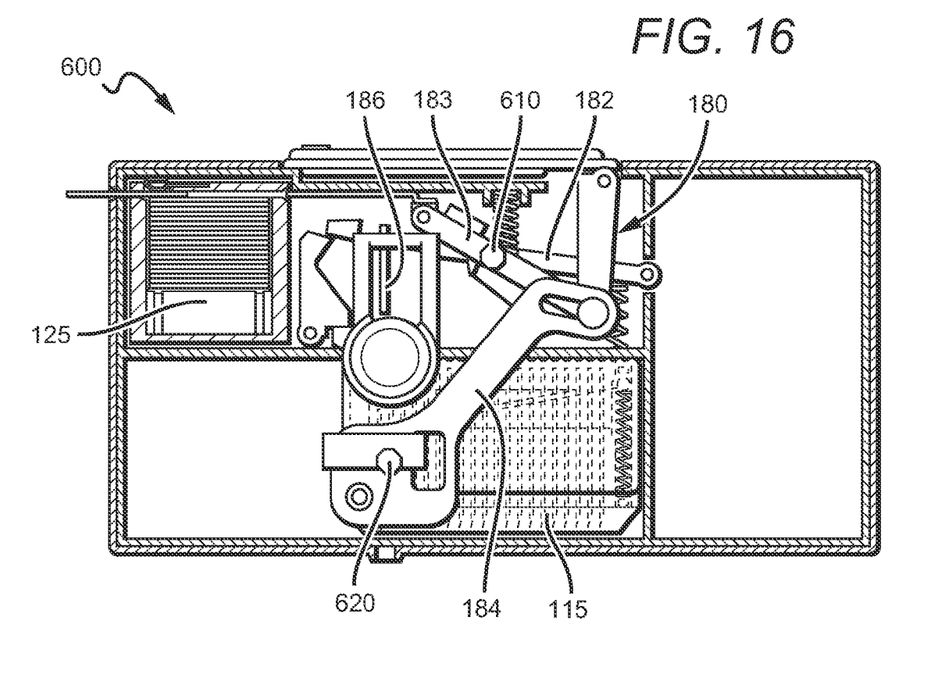
FIG. 16 is a side of an analyte device with a first and second disengagement control.

FIG. 16 shows an analyte testing device 600 that has a first disengagement control 610 and a second disengagement control 620. Control 610 operates to disengage link 182 from link 183, thus disengaging cartridge 125 from linkage mechanism 180. Control 620 operates to disengage link 184 from cartridge 115. In this manner, cartridges 115 and 125 can be disengaged from linkage mechanism 180, and thus can be used independently of one another.

Figure 17:
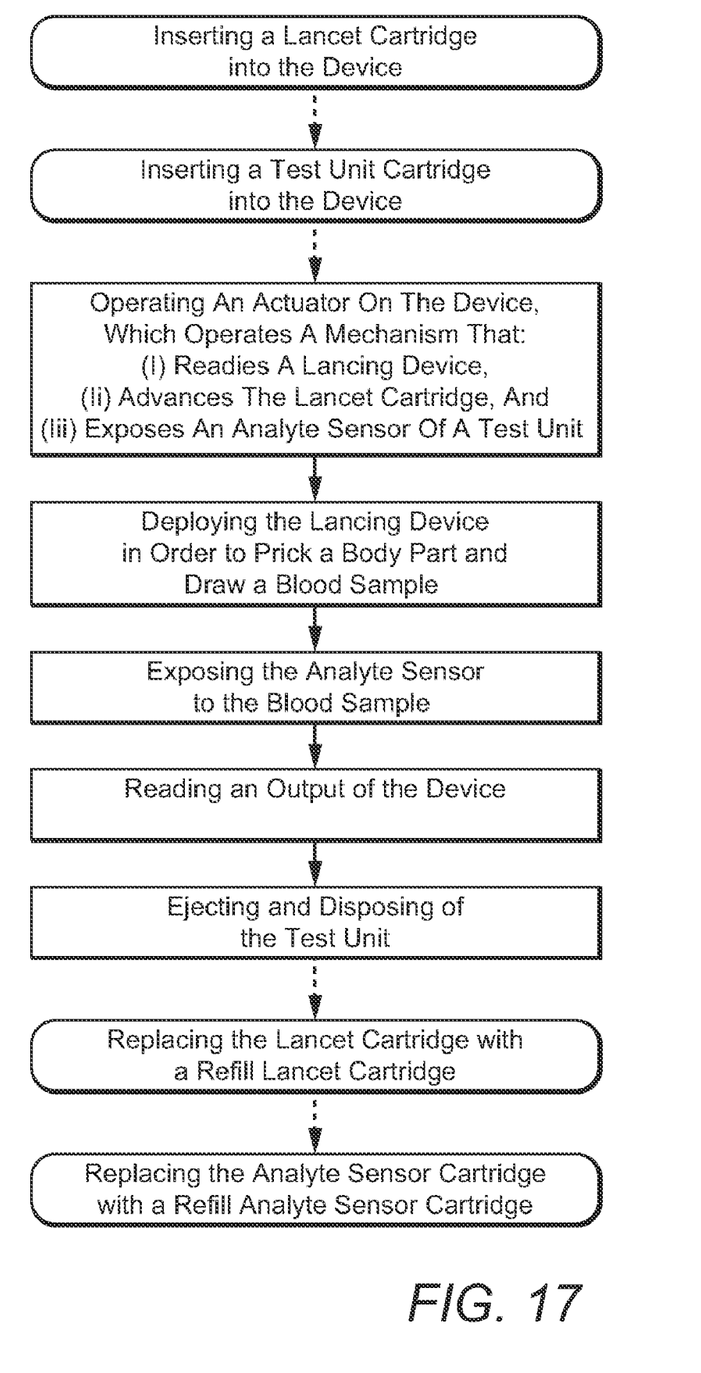
FIG. 17 is a schematic of one embodiment of a method of using the device of FIG. 1.

FIG. 17 shows a method of using device 100, comprising: inserting a lancet cartridge into the device; inserting a test strip cartridge into the device; operating an actuator on the device, which operates a mechanism that (i) readies a lancing device, (ii) advances the lancet cartridge, and (iii) exposes an analyte sensor of a test unit; deploying the lancing device in order to prick a body part and draw a blood sample; and exposing the analyte sensor to the blood sample. The method of FIG. 15 can optionally include the steps of: reading an output of the device; ejecting and disposing of the test unit; replacing the lancet cartridge with a refill lancet cartridge; and replacing the analyte sensor cartridge with a refill analyte sensor cartridge.

The first two and last two steps are displayed in round boxes and with dotted lines to indicate that these steps need not be repeated at every cycle of usage of the device. For example, in embodiments having twenty lancets and test strips per cartridge, the steps of inserting/removing cartridges need only be performed every twentieth cycle of use.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An analyte testing device, comprising:
a housing that houses an analyte sensor and a lancet;
a linkage mechanism at least partially disposed in the housing and having a first link coupled with the analyte sensor and a second link coupled with the lancet, wherein the first and the second links intersect one another at an angle on the linkage mechanism;
an actuator coupled with the linkage mechanism; and
wherein a single motion of the actuator in one direction moves (a) the first link and thereby exposes the analyte sensor at a first position of the housing, and (b) the second link and thereby advances the lancet for projection from a second position of the housing; and wherein the analyte sensor and the lancet are configured to move independently of each other.

2. The device of claim 1, wherein the analyte sensor is included in an analyte sensor cartridge.

3. The device of claim 1, wherein the analyte sensor is disposed in a test strip.

4. The device of claim 1, wherein the lancet is included in a lancet cartridge.

5. The device of claim 2, wherein the lancet is included in a lancet cartridge.

6. The device of claim 1, wherein the actuator comprises a manually operated lever.

7. The device of claim 1, wherein the mechanism is entirely manually operated.

8. The device of claim 1, wherein the mechanism is operated at least in part by a motor.

9. The device of claim 1, wherein the mechanism further comprises a hammer, and wherein the actuator cocks the hammer.

10. The device of claim 9, wherein the hammer is spring loaded.

11. The device of claim 9, wherein the linkage mechanism exposes the analyte sensor, advances the lancet for use, and cocks the hammer in a single motion.

12. The device of claim 11, wherein the single motion comprises operating a lever.

13. The device of claim 12, further comprising a motor configured to operate the lever.

14. The device of claim 12, wherein the lever comprises a manually-operated lever.

15. The device of claim 1, wherein exposing of the analyte sensor can be independently operated relative to advancing the lancet.

16. The device of claim 1, wherein the mechanism has a disengagement control that disengages operation of the actuator from exposing of the analyze sensor.

17. The device of claim 1, wherein the mechanism has a disengagement control that disengages operation of the actuator from advancement of the lancet.

18. The device of claim 1, wherein the first and second positions are separated by at least 5 mm.

* * * * *